United States Patent
Ben M'Barek et al.

(10) Patent No.: US 11,944,720 B2
(45) Date of Patent: Apr. 2, 2024

(54) METHOD AND DEVICE FOR PREPARING AN IMPLANT OBTAINED FROM A CULTURE OF STEM CELLS

(71) Applicant: CENTRE D'ETUDE DES CELLULES SOUCHES, Corbeil-Essonnes (FR)

(72) Inventors: Karim Ben M'Barek, Creteil (FR); Walter Habeler, Paris (FR); Christelle Monville, Champigny sur Marne (FR)

(73) Assignee: CENTRE D'ETUDE DES CELLULES SOUCHES (CECS), Corbeil-Essonnes (FR)

( * ) Notice: Subject to any disclaimer, the term of this patent is extended or adjusted under 35 U.S.C. 154(b) by 871 days.

(21) Appl. No.: 16/980,120

(22) PCT Filed: Mar. 12, 2019

(86) PCT No.: PCT/FR2019/050529
§ 371 (c)(1),
(2) Date: Sep. 11, 2020

(87) PCT Pub. No.: WO2019/175497
PCT Pub. Date: Sep. 19, 2019

(65) Prior Publication Data
US 2021/0023273 A1 Jan. 28, 2021

(30) Foreign Application Priority Data
Mar. 12, 2018 (FR) ...................... 18/52114

(51) Int. Cl.
| | | |
|---|---|---|
| *A61L 27/38* | (2006.01) | |
| *A61L 27/52* | (2006.01) | |
| *C12M 1/00* | (2006.01) | |
| *C12M 1/12* | (2006.01) | |
| *C12M 3/00* | (2006.01) | |
| *C12N 5/071* | (2010.01) | |
| *C12N 5/0735* | (2010.01) | |
| *C12N 5/079* | (2010.01) | |

(52) U.S. Cl.
CPC ....... *A61L 27/3834* (2013.01); *A61L 27/3813* (2013.01); *A61L 27/3869* (2013.01); *A61L 27/52* (2013.01); *C12M 21/08* (2013.01); *C12M 23/06* (2013.01); *C12M 23/38* (2013.01); *C12M 25/04* (2013.01); *C12N 5/0606* (2013.01); *C12N 5/0621* (2013.01); *C12N 5/069* (2013.01); *C12N 5/0697* (2013.01); *A61L 2400/06* (2013.01); *A61L 2430/16* (2013.01); *C12N 2502/02* (2013.01); *C12N 2502/085* (2013.01); *C12N 2502/28* (2013.01)

(58) Field of Classification Search
None
See application file for complete search history.

(56) References Cited

FOREIGN PATENT DOCUMENTS

| | | | |
|---|---|---|---|
| DE | 39 38 632 | 3/1991 | |
| EP | 2 671 539 | 12/2013 | |
| EP | 2671539 A1 * | 12/2013 | ............ C12M 23/06 |
| WO | 94/21204 | 9/1994 | |
| WO | WO-9421204 A1 * | 9/1994 | ............... A61F 2/14 |
| WO | 2017/096207 | 6/2017 | |
| WO | WO-2017096207 A1 * | 6/2017 | ............ C12M 23/22 |

OTHER PUBLICATIONS

Gagliardi et al. "Photoreceptor cell replacement in macular degneration and retinitis primentosa: A pluripotent stem cell-based approach" (2019) Progress in Retinal and Eye Research, vol. 71: 1-25 (Year: 2019).*
M'Barek et al. "Developing Cell-Based Therapies for RPE-Associated Degnerative Eye Diseases" in Pluripotent Stem Cells in Eye Disease Therapy (2019) Advances in Experiemental Medicine and Biology, vol. 1186: 55-97. (Year: 2019).*
M'Barek & Monville "Cell Therapy for Retinal Dystrophies: From Cell Suspension Formulation to Complex Retinal Tissue Bioengineering" (2019) Stem Cells International, vol. 2019, art. ID 4568979, 1-14. (Year: 2019).*
International Search Report for PCT/FR2019/050529 dated Jun. 19, 2019, 7 pages.
Search Report for FR 1852114 dated Nov. 26, 2018, 2 pages.
Nistor et al. "Three-dimentional early retinal progenitor 3D tissue constructs derived from human embryonic stem cells", Journal of Neuroscience Methods, Journal of Neuroscience Methods, Jun. 30, 2010, vol. 190, No. 1, 4 pages.
Written opinion of the international Search authority for PCT/FR2019/050529 dated Sep. 15, 2020 ( 5 pages).

* cited by examiner

*Primary Examiner* — Teresa E Knight
(74) *Attorney, Agent, or Firm* — NIXON & VANDERHYE

(57) ABSTRACT

Disclosed is a method for preparing an implant including a culture of cells on a membrane, the method including steps that consist of: securing the membrane to a mounting; placing the membrane in a recess of a housing providing two spaces having adjusted heights, above and below the membrane; injecting, into the spaces, a liquid capable of transforming into gel at a transport temperature lower than an injection temperature of the liquid; and bringing the housing to the transport temperature, so as to form an implant including the membrane and two layers of gel having adjusted thicknesses, on two opposite faces of the membrane, respectively.

20 Claims, 7 Drawing Sheets

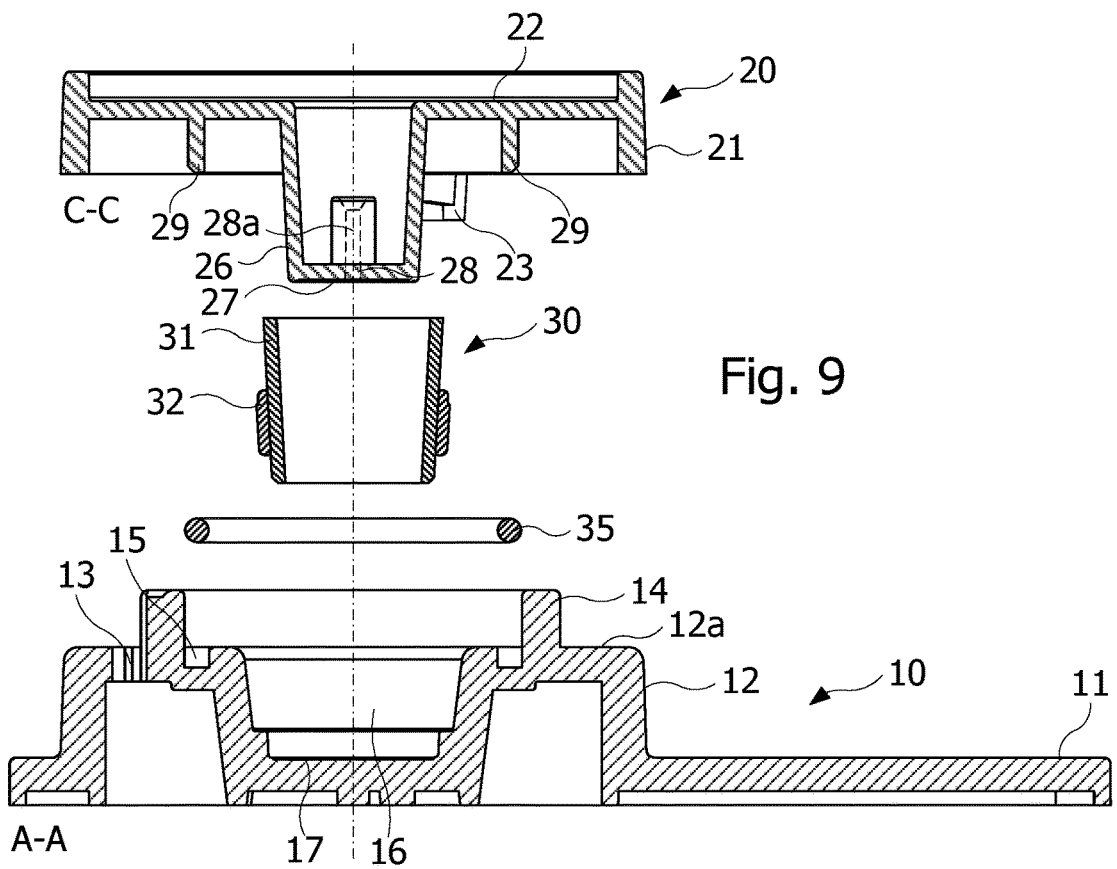
Fig. 9
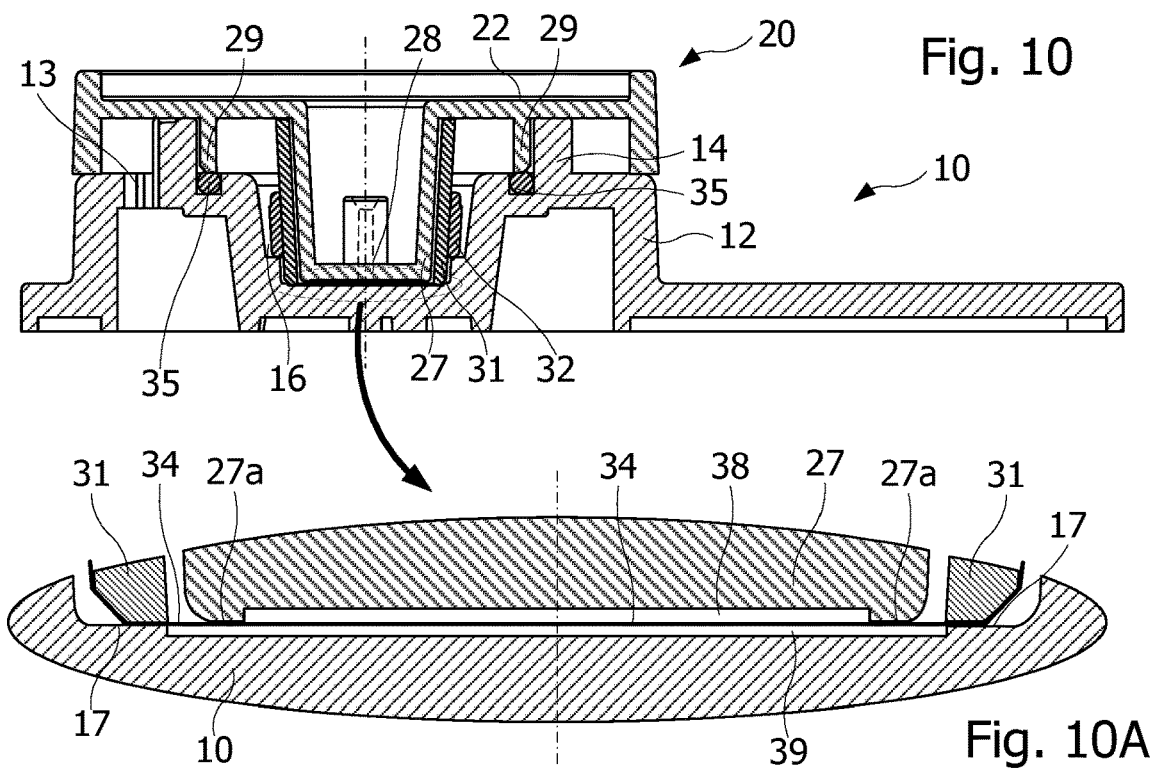
Fig. 10
Fig. 10A

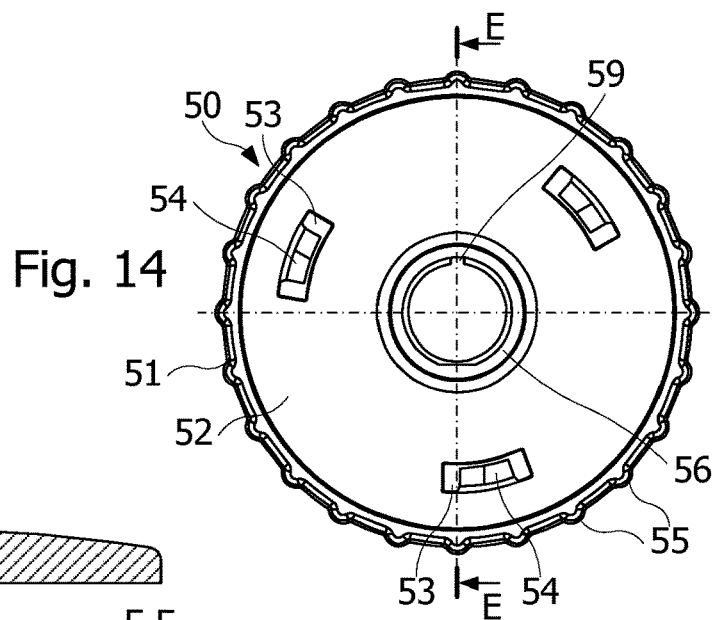
Fig. 14
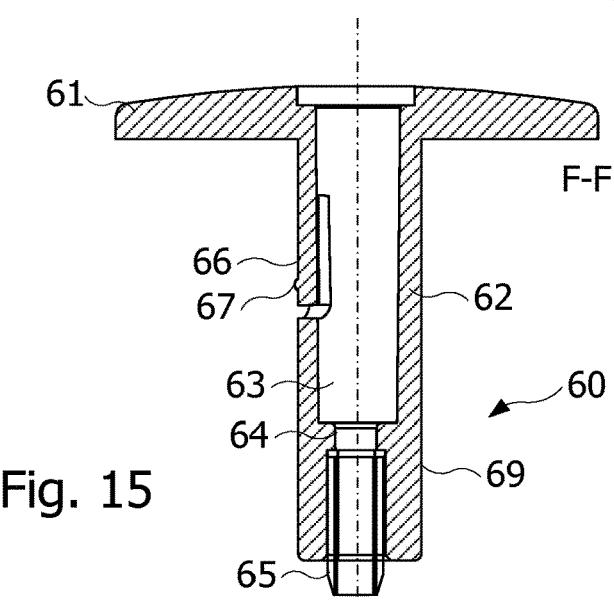
Fig. 15
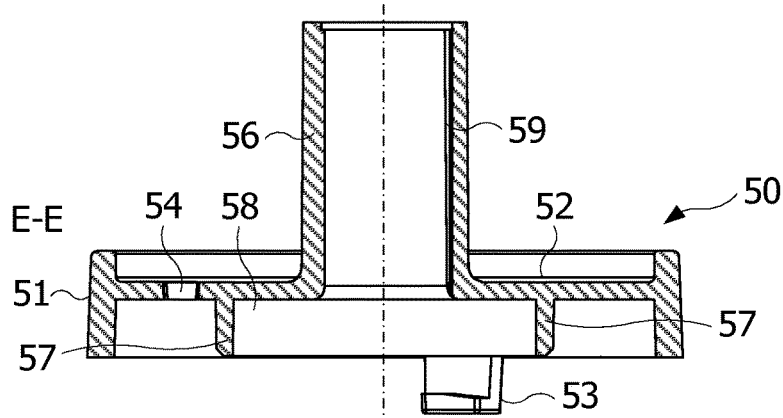
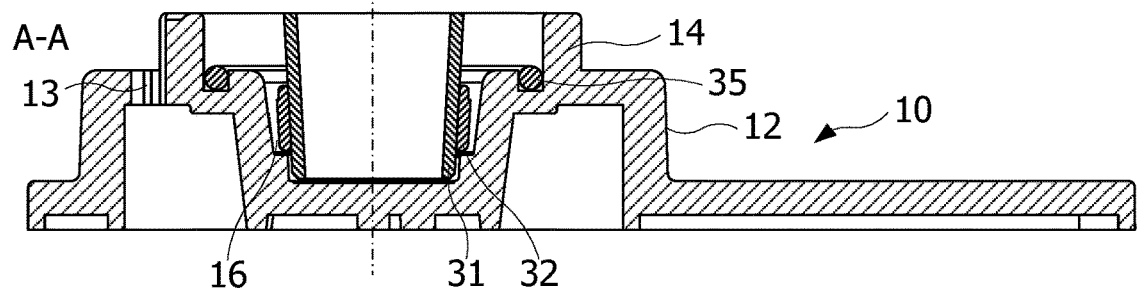

METHOD AND DEVICE FOR PREPARING AN IMPLANT OBTAINED FROM A CULTURE OF STEM CELLS

BACKGROUND OF THE INVENTION

Field of the Invention

The present invention relates to the preparation of an implantable graft, obtained from a culture of stem cells, in particular mammalian stem cells or any other type making it possible to obtain eye cells. The present invention is particularly applicable to the treatment of diseases of the retinal pigment epithelium and of the neural retina.

Description of the Related Art

The retina is the sensory layer that lines the posterior face of the eye, receives the image formed by the lens, translates this image into neuronal impulses which are transmitted to the brain by the optic nerve. The retina is a neuronal tissue that critically interacts with the retinal pigment epithelium which is necessary for its survival and proper functioning. The macula, constituting the central part of the retina, is enriched with photoreceptors capable of perceiving different colors and fine visual details. The macula is therefore crucial, especially for facial recognition and reading.

Many diseases can affect the retinal pigment epithelium or the neural retina and lead to impaired vision which can lead to blindness. Among these diseases, mention may in particular be made of hereditary or age-related macular degenerations, macular dystrophies, and retinitis pigmentosa. The retinal epithelium or the neural retina may also show lesions of traumatic or infectious origin. Recent research appears to show that damage to the retina can be delayed, stopped, or even repaired by transplanting retinal pigment epithelium cells or retinal cells into the subretinal space, which may prevent reduced capacity. visual effects caused by these diseases or improve them in the case of neural retinal cell transplants.

Various forms of grafts or transplantation techniques have been proposed in an attempt to preserve the retina. More recently, promising results have been obtained by transplanting a culture of retinal pigment epithelium cells obtained by differentiation of pluripotent stem cells, the cells being cultured on a membrane.

To prepare an implant from such a membrane, the membrane must be removed from a culture medium, and covered on both sides with a layer of gelatin. To this end, the gelatin layer is beforehand thinned and made uniform by removing an upper layer from it using a suitable cutting machine, called a "vibratome". The membrane is then placed on the thinned gelatin layer. The gelatin layer is again thinned to the desired thickness by removing a lower layer from it using the cutting machine. Finally, a drop of liquid gelatin (at 37° C.+ or −10° C.) is poured onto the cells cultured on the membrane, the gelatin being cold polymerized. The membrane, which is thus placed between two layers of polymerized gelatin, is then stored and transported as it is to the site of use. At the time of transplantation, the membrane must be manually cut to substantially the desired shape, usually under a microscope.

Transplantation is usually done using a syringe with a needle having a diameter smaller than the dimensions of the implant. As a result, the implant passes through the needle rolled-up on itself.

It turns out that this preparation process is very complex, requiring many manual manipulations carried out directly on the membrane, without the latter being protected. This results in many risks of alteration and contamination of the cell culture. The gelatin layers on either side of the membrane were also found to have varying thicknesses, which were furthermore non-uniform. Indeed, the precision of the cutting machine proves insufficient and the process used to form the upper gelatin layer generally leads to the production of a convex layer. The cutting machine is also cumbersome. Such variations in thickness lead to the risk that the implant will remain rolled-up on itself when it exits the injection needle. In the case of retinal pigment epithelium cells, the implant should be inserted under the retina. It should therefore be avoided that it is too thick when positioning it under the retina. Furthermore, since the membrane is separated from its culture support, it is difficult to visualize which side of the membrane the culture is on. There is a significant risk that the implant will be positioned on the wrong side after the transplant operation.

SUMMARY OF THE INVENTION

It is therefore desirable to provide a simplified method for making such an implant, while eliminating the risks of alteration and contamination of the culture. It is also desirable that the implant has a controlled thickness. It may also be desirable for the implant to have dimensions that are also controlled, in particular not linked to manual operations. It may also be desirable to eliminate implant positioning errors at the time of transplantation.

Embodiments relate to a method of preparing an implant comprising a culture of cells on a membrane, the method comprising the steps of: fixing the membrane on a support, placing the support in a housing recess providing two spaces having adjusted heights, above and below the membrane, injecting into the spaces a liquid capable of transforming into gel at a transport temperature lower than an injection temperature of the liquid, and bringing the housing to the transport temperature, so as to form an implant comprising the membrane and two layers of gel having adjusted thicknesses, respectively on two opposite faces of the membrane.

According to one embodiment, the method comprises a step of cutting the implant in the membrane and the two layers of gel, the membrane being fixed to the support and placed in the housing recess.

According to one embodiment, the method comprises a step of closing the housing of the housing recess receiving the membrane by an extraction cover, the extraction cover being configured to receive and guide a cutting tool configured to cut the implant in the membrane and the two gel layers.

According to one embodiment, the implant has an asymmetrical shape.

According to one embodiment, the spaces above and below the membrane are formed between the bottom of the housing recess and a preparation cover adapted to close the housing recess. According to one embodiment, the method comprises a step of replacing the preparation cover with a transport cover closing the housing recess in a sealed manner, when the liquid injected into the housing has polymerized into a gel.

According to one embodiment, the liquids injected into the upper and lower spaces are different, so that the upper gel layer is less rigid than the lower gel layer.

According to one embodiment, the cells arranged on the membrane are derived from pluripotent stem cells, from multipotent adult stem cells or else are obtained from primary cultures or from cell lines, or else correspond to a cell type of the implantation zone, or else they are simple epithelial cells of different subtypes, such as photoreceptors, ganglion cells, bipolar cells, amacrine cells, cells of the retinal pigment epithelium, endothelial cells. The human pluripotent stem cells used for the implementation of the invention do not require the destruction of a human embryo.

Embodiments can also relate to a device for preparing an implant from a cell culture on a membrane, the device comprising: a support holding the membrane, a housing comprising a housing recess for receiving the support associated with the membrane, the housing recess providing two spaces having adjusted heights, above and below the membrane, and a filling orifice for injecting a liquid into the two spaces, the liquid being able to transform into gel at a lower transport temperature at a liquid injection temperature, the device being configured to implement the method according to the invention.

According to one embodiment, the device comprises a preparation cover configured to close the housing recess with the support, the preparation cover delimiting with the membrane the upper space, the lower space being delimited by the bottom of the housing and the membrane, the preparation cover comprising a filling orifice opening into the upper space, the housing comprising a filling orifice opening into the lower space.

According to one embodiment, the device comprises a transport cover provided to close the housing recess in a sealed manner.

According to one embodiment, the device comprises an extraction cover provided to close the housing recess and comprising a conduit for the passage of a cutting tool configured to cut a piece of the membrane including cultured cells, the cut piece of membrane forming the implant.

According to one embodiment, the device comprises at least one of the following characteristics: the two spaces have a height of between 0.05 and 0.2 mm, or else between 0.13 and 0.17 mm, the implant has an area of between 10 and 20 $mm^2$. The membrane is an amniotic membrane, or a Bruch membrane, or a basal membrane, or a matrix of protein fibers such as collagen and/or fibrin fibers or a membrane made of a biocompatible synthetic material, biodegradable or not, the liquid turning into gel is a natural or synthetic biocompatible hydrogel, which is liquid at the internal temperature of the human body, the membrane support has a truncated cone shape with a large opening and a small opening, the membrane being fixed on the support so as to close the small opening, the cell culture being carried out on one face of the membrane arranged inside the support, the cutting tool is configured for cutting a piece of membrane with an asymmetrical shape.

Embodiments may also relate to a use of the device defined above, to produce an implant of cells cultured on a membrane.

BRIEF DESCRIPTION OF THE DRAWINGS

Examples of embodiments of the invention will be described in the following, without limitation in relation to the accompanying figures, among which:

FIG. 10A is a detailed sectional profile view of part of the handling device provided with the preparation cover, FIG. 14 is a top view of an implant extraction cover, according to one embodiment, FIGS. 15 and 16 are sectional side views, respectively exploded and not exploded, of the handling device provided with the extraction cover, and with a cutting device, according to one embodiment, the extraction cover shown in section along the plane EE shown in FIG. 14, the preparation device appearing in section along the plane AA shown in FIG. 3, and the cutting device appearing in section along the plane FF shown in FIG. 17.

DESCRIPTION OF THE PREFERRED EMBODIMENTS

Figure 1:
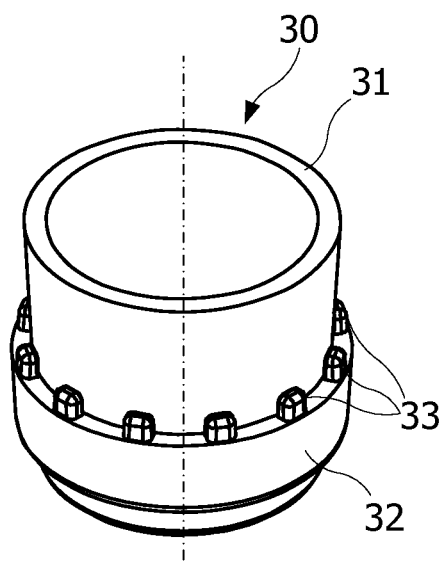
FIGS. 1 and 2 are perspective views and an exploded axial view of a cell culture support device, according to one embodiment.
Figure 2:
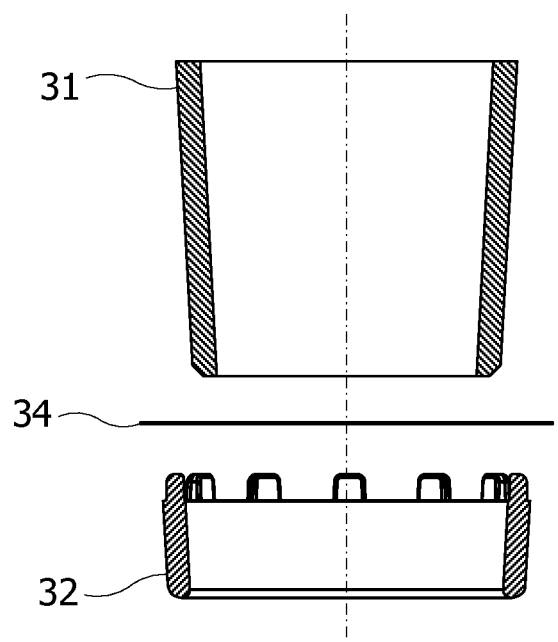

FIGS. 1 and 2 show a device 30 supporting a cell culture, according to one embodiment. The support device 30 comprises a tubular element 31, of truncated cone shape, for example with a circular section, on which a ring 32 engages. The tubular element 31 thus has, respectively at its two ends, two openings having different diameters or widths, the opening of smaller width being shown downwards in FIGS. 1 and 2.

The crown 32 also has a shape of truncated cone, the section of which has a shape identical to that of the tubular element 31. The edge of the wider opening of the crown 32 may include pins 33 extending axially. The pins make it easier to distinguish the openings of the crown 32 in order to engage the latter on the tubular element 31 in the correct direction.

The width of the crown 32 is such that the latter can slide only along a part of the tubular member 31, from the opening of smaller width of the tubular member 31. The cells are cultured on a membrane 34 which is fixed to the support device 30, being clamped between the tubular member 31 and the crown 32. The cells on the membrane 34 are thus located in the tubular member 31, the smaller width opening of the tubular member being closed by the membrane 34. Cell culture can be achieved by attaching membrane 34 to the end of tubular member 31.

If in the example of FIGS. 1 and 2, the support device has a circular section, any other section shape can be considered, such as a square, polygonal, rectangular, etc.

The membrane 34 may have a thickness of between 50 and 100 μm, and be made of a natural or synthetic material. Thus the membrane can be made from an amniotic membrane, a Bruch's membrane, a basal membrane, or a matrix of protein fibers such as collagen and/or fibrin fibers. It can also be made of a biocompatible synthetic material such as a biodegradable polymer. It is important that the cells in the culture adhere to the chosen membrane.

According to an exemplary embodiment, the cells of the culture are retinal pigment epithelium cells obtained from human pluripotent stem cells placed on a denuded amniotic membrane, then cultured for four weeks.

Figure 3:
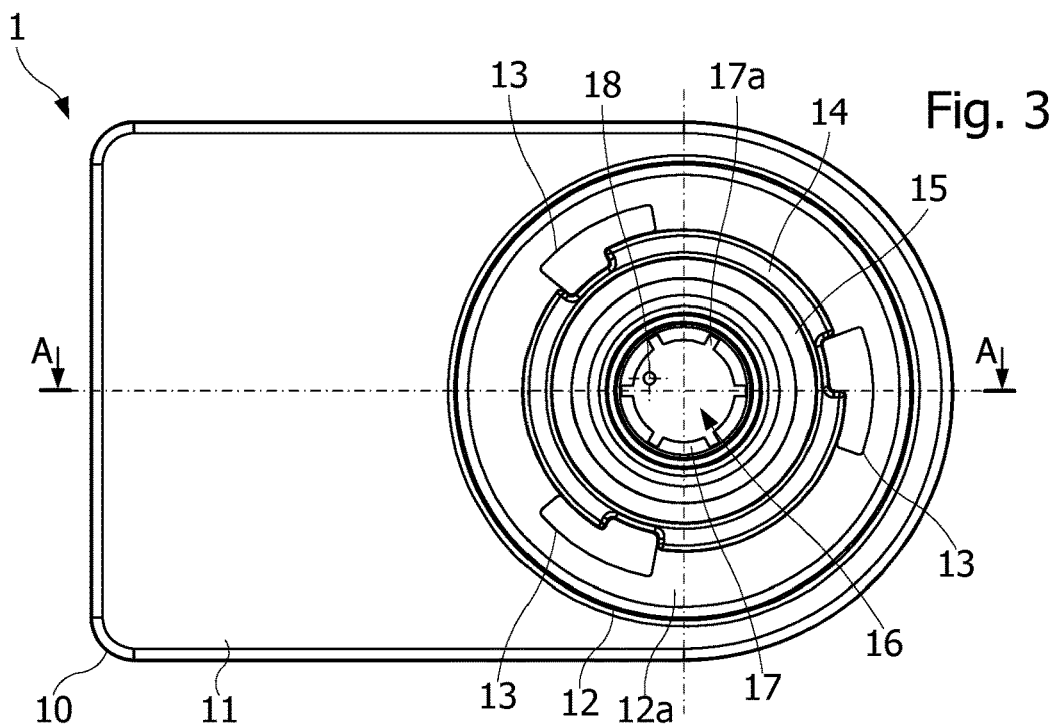
FIGS. 3 to 5 are, respectively a top view, a side view and a bottom view of a device for handling a cell culture, according to one embodiment.
Figure 4:
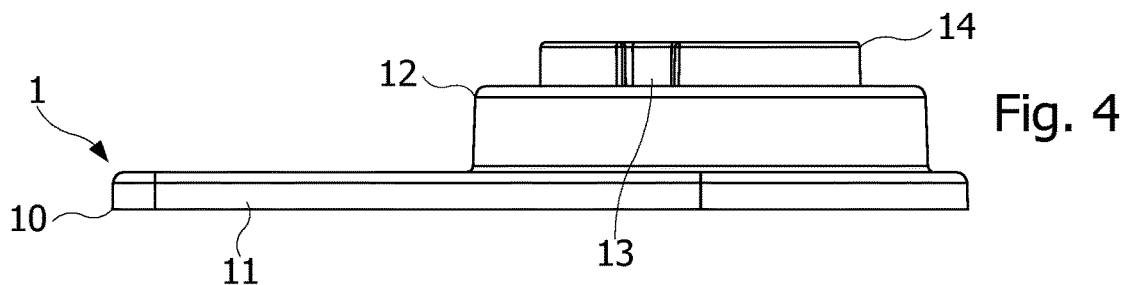
Figure 5:
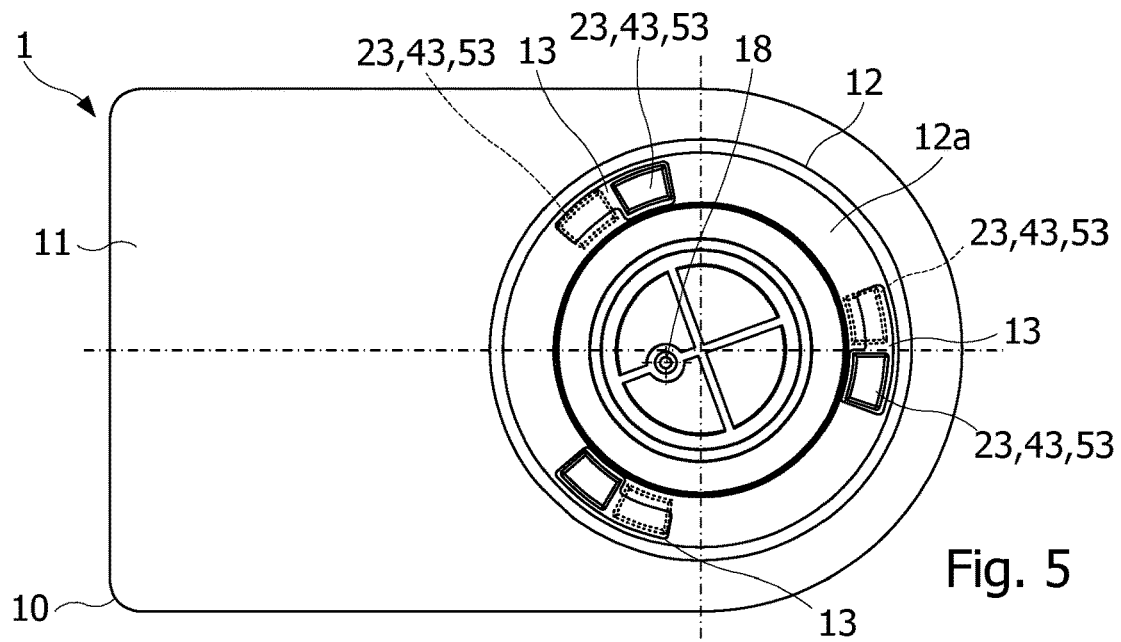

FIGS. 3 to 5 show a handling device 10 a cell culture, according to one embodiment. The handling device 10 comprises a housing recess 16 provided to receive the support device 30 and the membrane 34, and means for closing 15 and fixing 13 a cover making it possible to close the housing recess 16, in particular when the latter contains the support device. 30. The handling device 10 also includes a filling orifice 18 made in the bottom of the housing recess 16. The bottom of the housing recess 16 also has an annular rim 17.

In the example of FIGS. 3 to 5, the handling device 10 comprises a plate 11 integral with the housing recess 16. The housing recess 16 has a cylindrical shape comprising an outer edge 12 of tubular shape, an upper edge 12a flat, of annular shape, parallel to the plate 11, and an annular rib 14 axially extending the upper plane edge 12a. The housing recess 16 also has an annular groove 15 inside the rib 14, the annular groove surrounding the housing recess 16.

In the example of FIGS. 3 to 5, the fixing means 13 comprise openings 13 in the form of annular arcs, made in the upper plane edge 12a, and each comprising two parts of different widths.

Figure 6:
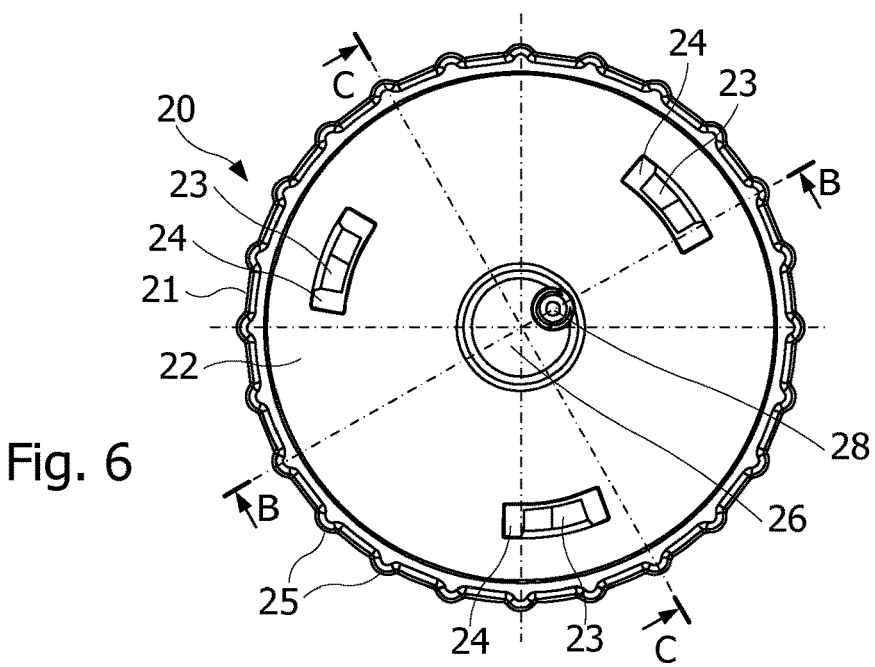
FIGS. 6 and 7 are, respectively a top view, a side view of a cover for preparing an implant, adapted to be fixed on the handling device, according to one embodiment.
Figure 7:
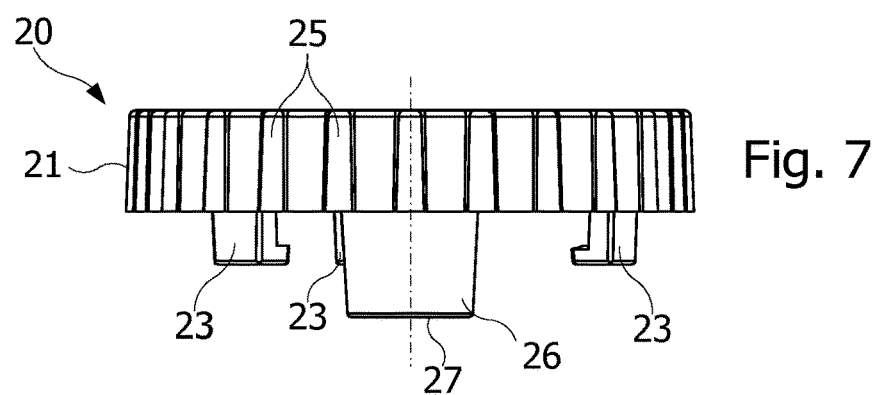
Figure 8:
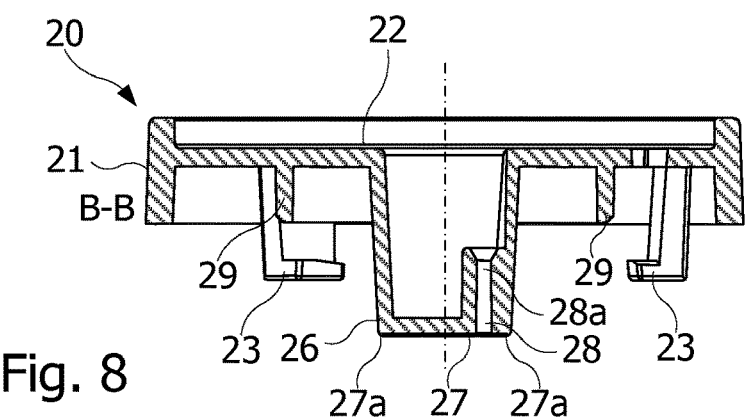
FIG. 8 is a side view of the preparation cover, in section along a plane BB shown in FIG. 6, FIGS. 9 and 10 are side views, respectively exploded and not exploded, of the handling device shown in section along the plane AA shown in FIG. 3, associated with the preparation cover shown in section along the plane CC shown in the FIG. 6.

FIGS. 6 to 8 show a preparation cover 20 of an implant, suitable for fixing to the handling device 10, according to one embodiment. The preparation cover 20 comprises an upper plate 22 of annular shape, extended on the outside by an outer ring 21, and on the inside, by a tubular extension 26, extending coaxially from the side of the lower face of the upper plate. 22. The preparation cover 20 also comprises fixing means 23 extending from the lower side of the cover and shaped to cooperate with the fixing means 13 of the handling device 10. The tubular extension 26 has a bottom 27 provided with a filling orifice 28, extending parallel to the upper plate 22. The preparation cover 20 also comprises an annular rib 29 extending from the underside of the cover, and provided to cooperate with the annular groove 15 formed in the handling device 10.

In the example of FIGS. 6 to 8, the fixing means 23 have the form of hooks provided to engage simultaneously in the widest part of the openings 13. The hooks 23 have an axial part extended by a radial part designed to lock in the narrowest part of the openings 13 by a rotational movement of the preparation cover 20 about its axis relative to the handling device 10. FIG. 5 shows the hooks 23 in solid lines engaged in the widest part of the openings 13, and in broken lines in the locking position, engaged in the narrowest part of the openings 13. To facilitate the rotation by hand of the cover 20, the outer ring 21 can be provided with notches 25. Openings 24 can be formed in the upper plate 22, directly above the radial portions of the hooks 23 for manufacturing reasons. The orifice 28 can be extended inside the tubular extension 26 by a pipe 28a in the form of a funnel.

FIGS. 9 and 10 show the assembly of the handling device 10 associated with the preparation cover 20 and enclosing the support device 30. It appears from these figures that when the cover 20 is locked on the handling device 10, the entire support device 30 can be enclosed in the housing recess 16. The sealing of the closure of the housing recess 16 is ensured by an O-ring 35 disposed in the annular groove 15, the O-ring 35 being compressed by the annular rib 29 formed under the cover 20.

FIG. 10A shows in detail the bottom of housing recess 16, with the lower end 27 of the tubular extension 26, the lower end of the support device 30 and the membrane 34 supporting the cell culture. It appears in FIG. 10A that the annular rim 17 formed at the bottom of the housing recess 16 keeps the support device 30, and therefore the membrane 34, away from the bottom of the housing recess 16, thus delimiting between the bottom of the housing recess 16 and the membrane an empty space 39 in the form of a disc into which the filling orifice 18 opens.

Furthermore, the tubular extension 26 has a length such that when the cover 20 is locked on the handling device 10, the lower end 27 of the tubular extension 26 comes into contact with the upper face of the membrane 34. The lower end 27 of the tubular extension 26 has an annular flange 27a, leaving between the lower end 27 of the tubular extension 26 and the membrane 34 an empty space 38 in the form of a disc into which the filling orifice 28 opens.

According to one embodiment, the empty spaces 38, 39 which have a predefined height, are filled with a substance, such as a natural or synthetic biocompatible hydrogel, exhibiting a liquid state at the temperature of the interior of the human body, around 37° C., and which gel polymerizes at a lower temperature.

According to an exemplary embodiment, one of the spaces 38, 39, is filled with the substance in liquid form. The handling device 10 is then cooled so that the liquid polymerizes into a gel. The other space 38, 39 is filled with the substance in liquid form and the handling device 10 is cooled again. When filling the lower space 39, for example using a micropipette, through the orifice 18, the air initially present in this space is evacuated through notches 17a formed in the annular rim 17 (FIG. 3). When filling the upper space 38 through the orifice 28, the air present in this space is discharged through the space between the support device 30 and the tubular extension 26.

Thus, the handling device 10 combined with the preparation cover 20 makes it possible to prepare an implant comprising the membrane 34 supporting the cells to be transplanted and covered on each side with a layer of gel. This operation does not require separating the membrane 34 from its support 30. The gel thicknesses on each side of the membrane are fixed and defined so that the implant can be rolled-up on itself and thus pass through the needle of a syringe used for transplantation, and having a diameter from 1.8 to 2.2 mm. The gel thicknesses on each side of the membrane 34 are also chosen so that the implant regains a substantially planar shape, naturally without manipulation, at the exit of the needle from the syringe. After the transplantation, the substance in the gel state before and during the transplant gradually turns to a liquid state and mixes with body fluids.

In one embodiment, the lower space 39 is filled with the substance first, then the upper space 38 is filled before the substance injected into the lower space 39 is fully polymerized. The quantity of the substance injected through the two orifices 18, 28 can be adjusted so as to prevent the membrane 34 from bulging. The concentration of the substance injected into the upper space 38 may be less than that injected into the lower space 39, so that the implant is less rigid and therefore can bend more easily towards the side of the membrane 34 supporting the culture than to the other side.

According to an exemplary embodiment, the substance used to fill the spaces 38, 39, is gelatin which is in the gel state at a temperature below 7° C. and in the liquid state at 37° C. The height of the spaces 38, 39, that is to say the thickness of the gel layer on each side of the membrane 34 is between 0.05 and 0.2 mm, and preferably between 0.13 and 0.17 mm. The diameter of the orifices 18, 28 may be 1 mm (to within + or −20%). The gelatin injected into the lower space 39 is diluted to a concentration of 8% (+ or −2%) in physiological serum, and is left to polymerize for 3 minutes at a temperature of 4° C. (+ or −3° C.), complete polymerization being obtained after 5 minutes at these temperatures. The gelatin injected into the upper space 38 is diluted to a concentration of 5% (+ or −2%) in physiological saline. The entire handling device 10 and cover 20, including the culture, is then maintained at a temperature below 7° C. for more than 5 minutes.

Figure 11:
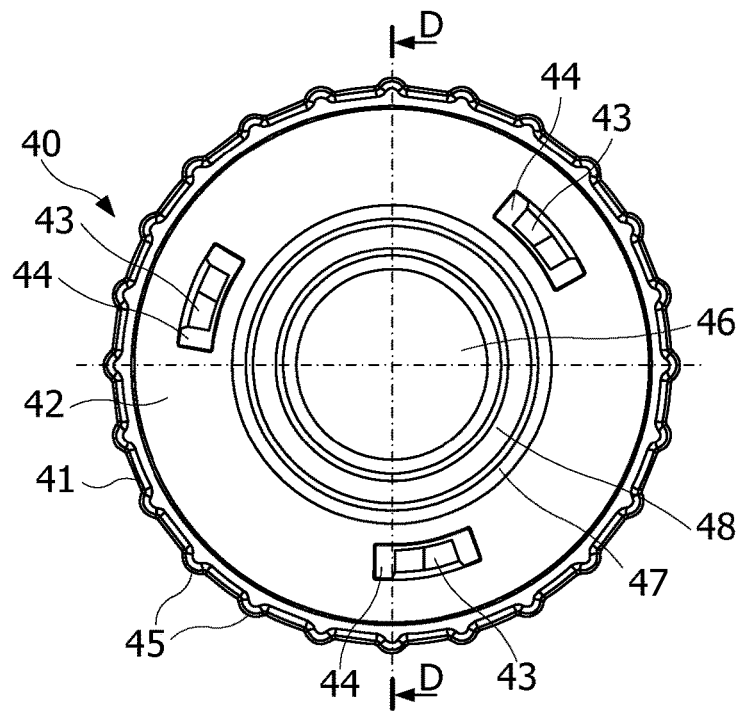
FIG. 11 is a top view of a transport cover, suitable for attaching to the handling device, according to one embodiment.
Figure 12:
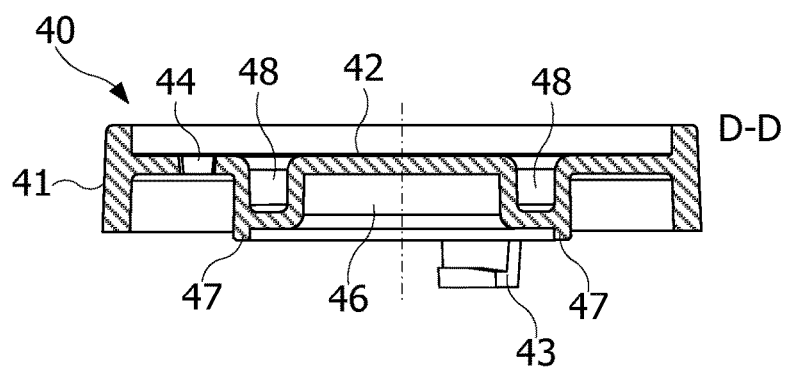
FIG. 12 is a side view of the transport cover, in section along the plane DD shown in FIG. 11.
Figure 13:
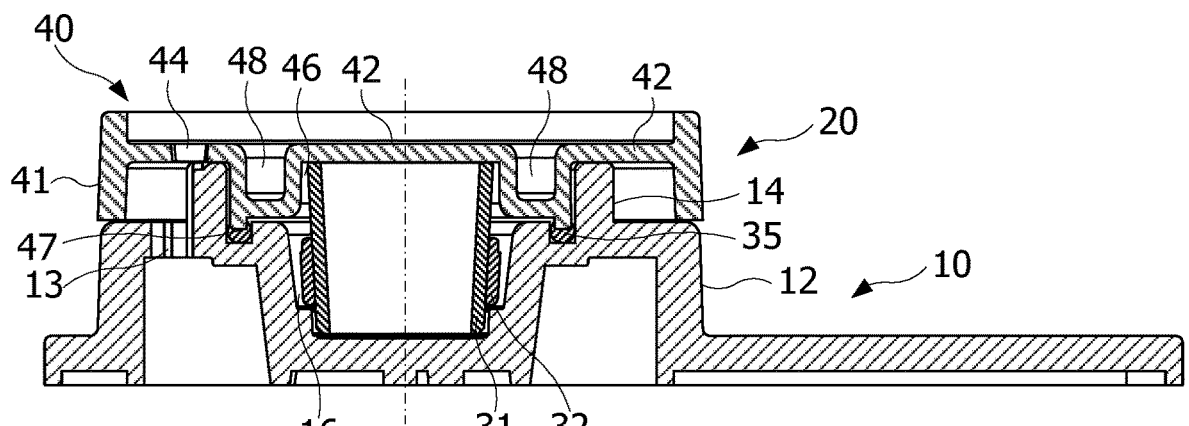
FIG. 13 is a view of the handling device in section along the plane AA shown in FIG. 3, associated with the transport cover in section along the plane DD shown in FIG. 11.

FIGS. 11 and 12 show a transport cover 40, adapted to be fixed on the handling device 10, according to one embodiment. FIG. 13 shows the transport cover 40 fixed to the handling device 10. Once the required substance has been injected into spaces 38, 39 and has polymerized into a gel by refrigeration, the preparation cover 20 is removed and replaced with the transport cover 40. The transport cover 40 associated with the support 30 and the handling device 10 secures the implant during transport in order to prevent any dissociation of the gelatin layers, in particular under the effect of vibrations.

A suitable liquid can be used beforehand to fill the volume above the gel layer in the tubular element 31 of the support 30, in particular in order to keep the gel layer in a humid environment. This liquid can be, for example, a liquid used for the transport of human corneas such as STEM ALPHA. 1® marketed by the company STEM ALPHA. Thus, the handling device 10 associated with the transport cover makes it possible to transport the implant to the site where it is to be transplanted and to keep it cold (at a temperature below 10° C.) until the time of transplantation.

The transport cover 40 has a shape similar to that of the preparation cover 20, but without a tubular extension 26. Thus, the cover 40 comprises an upper plate 42 in the form of a disc, extended on the outside by an outer ring 41. The transport cover 40 also comprises fixing means 43 extending from the lower side of the cover and shaped to cooperate with the fixing means 13 of the handling device 10. The transport cover 40 also comprises an annular rib 47 extending from the underside of the cover, and provided to cooperate with the O-ring 35 disposed in the annular groove 15 formed in the handling device 10, to seal the closing of the housing recess 16. Thus, the housing recess 16 is sealed, the filling orifice 18 being closed by the gel.

In the example of FIGS. 11 to 13, the fixing means 43 have the form of hooks provided to engage simultaneously in the widest part of the openings 13. The hooks 43 have an axial part extended by a radial part provided to lock in the narrowest part of the openings 13 by a rotational movement of the transport cover 40 about its axis relative to the handling device 10. To facilitate the rotation by hand of the cover 40, the outer ring 41 can be provided with notches 45. Openings 44 may be formed in the upper plate 42, directly above the radial portions of the hooks 43 for manufacturing reasons. The plate 42 may include an annular groove 48 forming on the inside of the cover an annular rim ensuring the retention of the upper part of the support 30.

Figure 16:
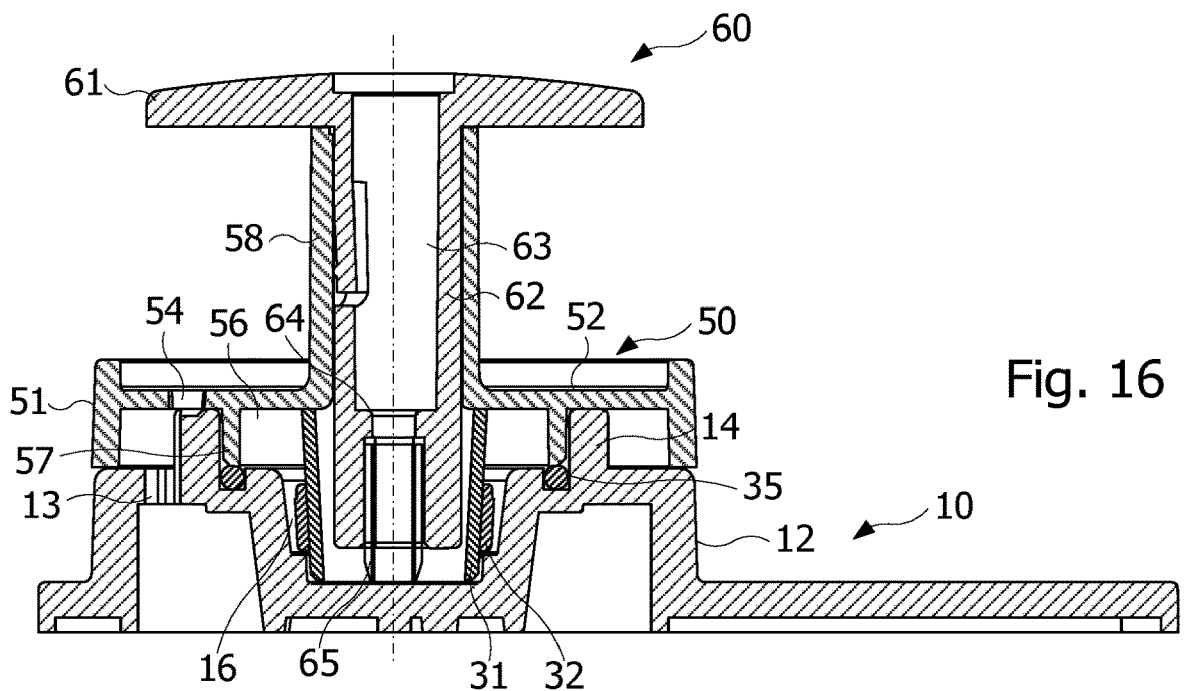

FIG. 14 shows an extraction cover 50 of the implant, according to one embodiment. FIGS. 15 and 16 show the handling device 10 provided with the extraction cover 50, and a cutting device 60, according to one embodiment. Once at the transplant site, the transport cover 40 is removed and replaced with the extraction cover 50. The cutting device 60 is inserted into the extraction cover 50 to remove the implant by cutting a piece of the membrane supporting the cell culture to be implanted and covered on both sides with the gel layer.

The extraction cover 50 has a shape similar to that of the preparation cover 20, in which the lower tubular extension 26 is replaced by an upper tubular extension 56 forming a tubular duct passing through the cover 50, allowing the passage of the cutting device. 60. Thus, the extraction cover 50 comprises an upper plate 52 of annular shape, extended on the outside by an outer ring 51. The extraction cover 50 also comprises fixing means 53 extending from the lower side of the cover and shaped to cooperate with the fixing means 13 of the handling device 10. The extraction cover 50 also comprises an annular rib 57 extending from the underside of the cover, and provided to cooperate with the O-ring 35 disposed in the annular groove 15 formed in the handling device 10, to seal the closing of the housing recess 16. The annular rib 57 defines a housing 58 for receiving the upper part of the support device 30.

In the example of FIGS. 14 to 16, the fixing means 53 have the form of hooks intended to engage simultaneously in the widest part of the openings 13. The hooks 53 have an axial part extended by a radial part designed to lock in the narrowest part of the openings 13 by a rotational movement of the extraction cover 50 about its axis relative to the handling device 10. To facilitate the rotation by hand of the cover 50, the outer ring 51 can be provided with notches 55. Openings 54 may be formed in the upper plate 52, in line with the radial portions of the hooks 53 for manufacturing reasons.

The upper tubular extension 56 is provided to receive the cutting device 60. The cutting device 60 comprises an upper plate 61 in the form of a disc, the lower face of which is extended axially by a tubular extension 62 provided with an axial central duct passing through 63 comprising a shoulder 64 against which bears a cutting tool 65 engaged through the lower opening of the axial duct 63.

In the example of FIG. 15, the upper tubular extension 56 comprises an axial rib 69 provided to cooperate with a groove formed in the internal wall of the axial duct 63, so as to force the angular orientation of the cutting device 60 by relative to the cover 50 at a precise angle. The tubular extension 62 may include a lug 67 formed in the vicinity of the free end of an axial tab 66. The lug 67 is provided so that at the end of the travel of the cutting device 60 in the cover 50, the lug 67 is erased by exerting a friction on the upper tubular extension 56. Thus the operator is obliged to press on the plate 61 until it is in abutment against the upper edge of the upper tubular extension 56, which makes it possible to ensure that the cutting tool 65 has indeed passed through the membrane 34 and its two gel layers. Indeed, as shown in FIG. 16, the cutting tool 65 comes into contact with the bottom of the housing recess 16 when the plate 61 abuts against the upper edge of the upper tubular extension 56.

Figure 17:
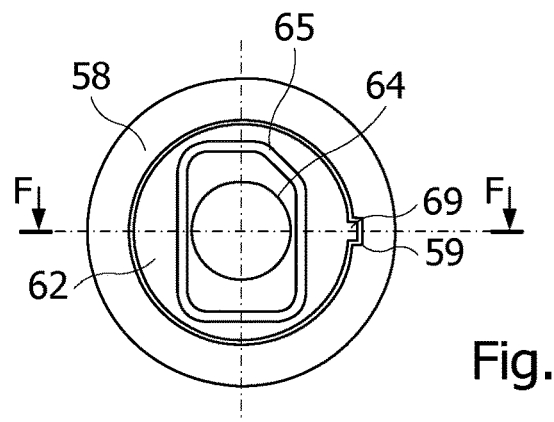
FIG. 17 is a detailed axial view from below of the lower end of the cutting device and part of the extraction cover.

FIG. 17 shows in more detail the lower end of the cutting device 60, and in particular the radial rib 69 which cooperates with the radial groove 59 of the cover 50 and the shape of the cutting tool 65. The cutting tool 65 is in the form of a tubular shaped cookie cutter, with a sharp lower edge for cutting a piece of the membrane 35 supporting the culture of cells to be implanted covered on both sides with a layer of gel. The cutting tool 65 is used to cut a piece of membrane having a non-symmetrical shape, so as to be able to determine on which side of the implant the cell culture is located. This arrangement allows the implant to be placed correctly in the patient's body, especially if it is to be placed on a surface. The extraction cover 50 thus provides guidance and orientation functions for the cutting tool 65.

In the example of FIG. 17, the cutting tool 65 is used to cut a substantially rectangle-shaped piece of implant with one corner removed to give it an unsymmetrical shape. The orientation of the cutting tool 65 obtained by virtue of the radial rib 69 which cooperates with the radial groove 59 of the cover 50, can be defined so that the blade of the cutting tool is at a distance from the filling orifice 18.

Figure 18:
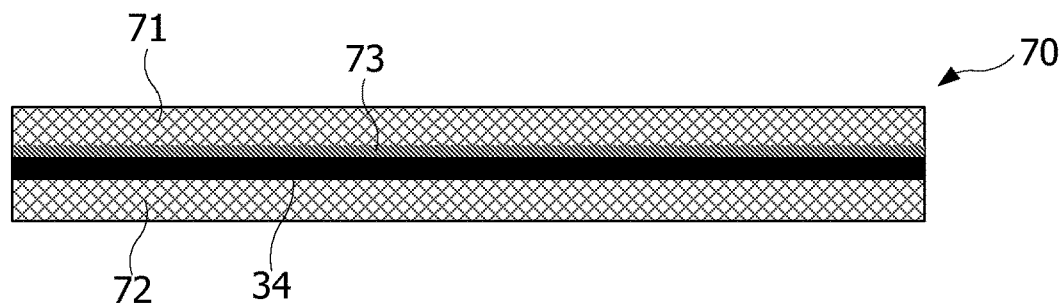
FIG. 18 is a schematic sectional view of an implant obtained by the method according to one embodiment of achievement.

FIG. 18 shows the implant 70 extracted from the membrane, obtained after the cutting operation using the cutting device 60. The implant 70 comprises the two layers of gel 71, 72 covering the membrane 34 on one side and the cell culture 73 formed on the membrane 34 on the other side.

When removing the cutting tool 60 from the extraction cover 50, it may happen that the implant 70 thus cut remains in the cutting tool 50. As the cutting device 60 and the cutting tool 65 have a tubular shape, it is possible to introduce a rod through the upper opening of the axial duct 63 through the plate 61, to push the implant 70 out of the cutting tool 65, the shank having a diameter smaller than that of the shoulder 64. If the implant 70 remains in the housing recess 16, it can be extracted from the latter using a spatula.

For an implant of human retinal pigment epithelium cells, the cutting tool 65 makes it possible to cut a piece of membrane 34 of 2 to 6 mm by 1.2 to 4 mm, for example of 5 by 3 mm or of 2.5 by 1.5 mm, i.e. an area of between 10 and 20 mm$^2$, for example 15 mm$^2$ (these values may vary in proportions of 20%). These dimensions make it possible to extract from the membrane 34 an implant comprising a few hundred thousand cells.

The implant 70 thus obtained has a perfectly controlled thickness and dimensions. It can be observed that throughout the preparation and transport of the implant 70, until its extraction at the time of carrying out the transplantation, the membrane 34 remains fixed to its support 30. This avoids any risk of deterioration of the cell culture. The periods when the housing containing the membrane associated with its support is open are limited to the steps of changing the cover and to the step of cutting the implant. The risks of contamination of the implant therefore remain limited. In addition, the fact of keeping the membrane 34 fixed to its support 30 until the implant 70 is cut, and of providing an asymmetrical shape for the implant, makes it possible to preserve the memory of the face of the membrane supporting the culture of cells until the transplant operation. Moreover, the only tools which may be necessary in addition to the elements previously described are limited to a push rod for, if necessary, to bring out the implant from the cutting tool 65, the transplant syringe and a spatula to catch and place the implant in the syringe.

It will be clear to those skilled in the art that the present invention is susceptible of various variant embodiments and various applications. In particular, the invention is not limited to a housing in which the gel layers are defined between a housing recess and a cover. In fact, provision may be made to use a housing provided with a slot in which the membrane separated from its support is inserted, the slot having a calibrated width.

It is also not necessary to have a transport cover. In fact, provision may be made for placing the case used for molding the gel layers (handling device 10+the preparation cover 20) in a sealed bag, the gel layers not being able to flow through the orifices 18, 28 as long as the housing is kept at a sufficiently low temperature. It can also be envisaged to seal the orifices 18, 28 in a sealed manner.

It is also not necessary to have an extraction cover. Indeed, the piece of membrane to be implanted can be cut and extracted directly from the housing recess 16 using a punch. It can also be cut, for example, with a scalpel or scissors.

It is also not necessary for the implant to have an asymmetrical shape. Other ways can be easily imagined to locate the face of the membrane supporting cell culture. Thus, for example, the gel layer formed on one of the two faces of the membrane can be colored by means of a dye mixed with the liquid injected through one of the two orifices 18, 28.

It should also be noted that the preparation of the implant using the preparation cover 20 and the use of the implant after cutting the membrane can be carried out at geographically remote sites. Therefore, the step of removing the implant by cutting the membrane may not be performed.

It may also be provided to simultaneously fill the upper 38 and lower 39 spaces on each side of the membrane 34, for example by providing lateral passages in the rim 27*a* (or by removing this rim) and in the tubular element 31 of the support. 30. In this case, only one of the two orifices 18, 28 is necessary.

Furthermore, any other means of fixing the covers 20, 40, 50 on the preparation device 10 than that described can be envisaged. Thus, the covers 20, 40, 50 can also be screwed onto the preparation device 10 or be attached to the latter by clipping.

The invention may be applied to implants other than retinal pigment epithelium cell implants. Indeed, the invention can be applied to the transplantation of cells of the retina of various subtypes and used alone or in combination (for example for the retina: photoreceptors, ganglion cells, bipolar cells, amacrine cells, retinal pigment epithelium cells, endothelial cells). These cells can be combined in monolayers or in multi-layered layers so as to reconstruct an artificial retina. It may also be, in particular, cells of the cornea or any other type of epithelial cell. More generally, the invention can be applied to any type of epithelium or cell culture in a monolayer on a biological or synthetic membrane.

The invention claimed is:

1. A method of preparing an implant (70) comprising a culture of cells (73) on a membrane (34), the method comprising the steps of: fixing the membrane on a support (30), disposing the support in a housing recess (16) of a housing (10, 20) leaving two spaces (38, 39) having adjusted heights, above and below the membrane, injecting into the spaces a liquid capable of transforming into gel at a temperature of transport below an injection temperature of the liquid, and bringing the housing to the transport temperature, so as to form an implant comprising the membrane and two layers of gel (71, 72) having adjusted thicknesses, respectively, on two opposite faces of the membrane.

2. The method according to claim 1, comprising a step of cutting the implant (70) in the membrane (34) and the two layers of gel (71, 72), the membrane being fixed to the support (30) and disposed in the housing recess (16).

3. The method according to claim 2, comprising a step of closing the housing recess (16) of the housing (10) receiving the membrane by an extraction cover (50), the extraction cover being configured to receive and guide a cutting tool

(60) configured to cut the implant (70) in the membrane (34) and the two layers of gel (71, 72).

4. The method according to claim 2, wherein the implant (70) has an asymmetrical shape.

5. The method according to claim 2, wherein the spaces (38, 39) above and below the membrane (34) are formed between the bottom of the housing recess (16) and a preparation cover (20) suitable for closing the housing recess.

6. The method according to claim 1, comprising a step of closing the housing recess (16) of the housing (10) receiving the membrane by an extraction cover (50), the extraction cover being configured to receive and guide a cutting tool (60) configured to cut the implant (70) in the membrane (34) and the two layers of gel (71, 72).

7. The method according to claim 6, wherein the implant (70) has an asymmetrical shape.

8. The method according to claim 6, wherein the spaces (38, 39) above and below the membrane (34) are formed between the bottom of the housing recess (16) and a preparation cover (20) suitable for closing the housing recess.

9. The method according to claim 1, wherein the implant (70) has an asymmetrical shape.

10. The method according to claim 9, wherein the spaces (38, 39) above and below the membrane (34) are formed between the bottom of the housing recess (16) and a preparation cover (20) suitable for closing the housing recess.

11. The method according to claim 1, wherein the spaces (38, 39) above and below the membrane (34) are formed between the bottom of the housing recess (16) and a preparation cover (20) suitable for closing the housing recess.

12. The method according to claim 1, comprising a step of replacing the preparation cover (20) by a transport cover (40) closing the housing recess (16) in a sealed manner, when the liquid injected into the housing recess is gel polymerized.

13. The method according to claim 1, in which the liquids injected into the upper (38) and lower (39) spaces are different, so that the upper gel layer (71) is less rigid than the layer lower gel (72).

14. The method according to claim 1, in which the cells arranged on the membrane are chosen among cells derived from pluripotent stem cells, from multipotent adult stem cells from primary cultures from cell lines, to a cell type corresponding to cells of the implantation area, or are epithelial cells, photoreceptors, ganglion cells, bipolar cells, amacrine cells, retinal pigment epithelial cells, and endothelial cells.

15. A device for preparing an implant from a cell culture on a membrane, the device comprising: a support (30) holding the membrane (34), a housing (10, 20) comprising a housing recess (16) for receiving the support associated with the membrane, the housing providing two spaces (38, 39) having adjusted heights, above and below the membrane, and a filling orifice (18, 28) for injecting liquid into the two spaces, the liquid being capable of transforming into a gel at a transport temperature below an injection temperature of the liquid, the device being configured to implement the method according to claim 1.

16. The device according to claim 15, comprising a preparation cover (20) configured to close the housing recess (16) with the support (30), the preparation cover delimiting with the membrane (34) the upper space (38), the lower space (39) being delimited by the bottom of the housing recess and the membrane, the preparation cover comprising a filling orifice (28) opening into the upper space, the housing comprising a filling orifice (18) opening into the space inferior.

17. The device according to claim 15, comprising a transport cover (40) provided to close the housing (16) in a sealed manner.

18. The device according to claim 15, comprising an extraction cover (50) provided to close the housing recess (16) and comprising a tubular extension (56) for the passage of a cutting tool (60) configured to cut a piece of the membrane (34) including cultured cells, the cut piece of membrane forming the implant (70).

19. The device according to claim 15, comprising at least one of the following characteristics:
 the two spaces (38, 39) have a height of between 0.05 and 0.2 mm,
 the implant (70) has an area of between 10 and 20 mm2
 the membrane (34) is an amniotic membrane, or a Bruch's membrane, or a basal membrane, or a matrix of protein fibers, or a membrane made of a biocompatible synthetic material, biodegradable or not,
 the liquid turning into gel is a natural or synthetic biocompatible hydrogel, which is liquid at the internal temperature of the human body,
 the membrane support (30) has a truncated cone shape with a large opening and a small opening, the membrane being attached on the support so as to close the small opening, the cell culture being carried out on one face of the membrane disposed inside the support, the cutting tool (60) is configured to cut a piece of membrane of asymmetric shape.

20. A method for producing an implant of cells cultured on a membrane (34) using the device according to claim 15.

* * * * *